United States Patent [19]

Bagli et al.

[11] Patent Number: 4,900,829

[45] Date of Patent: Feb. 13, 1990

[54] 2,4-DISUBSTITUTED-5-CYANO-1,6-DIHYDRO-6-OXO-1-PYRIMIDINEACETIC ACID ALDOSE REDUCTASE INHIBITORS

[75] Inventors: Jehan F. Bagli; John W. Ellingboe, both of Princeton; Thomas R. Alessi, Flemington, all of N.J.

[73] Assignee: American Home Products Corporation, New York, N.Y.

[21] Appl. No.: 221,588

[22] Filed: Jul. 20, 1988

Related U.S. Application Data

[62] Division of Ser. No. 61,831, Jun. 12, 1987, Pat. No. 4,786,638.

[51] Int. Cl.$^4$ ............................................. C07D 239/22
[52] U.S. Cl. ..................................... 544/319; 544/298; 544/319
[58] Field of Search ............... 544/319, 321, 326, 329, 544/295, 298, 319

[56] References Cited

U.S. PATENT DOCUMENTS 4,505,910  3/1985  Bagli ..................................... 514/26
4,568,693  2/1986  Sestanj et al. ......................... 514/524
4,786,638  11/1988  Bagli et al. ............................ 514/252

OTHER PUBLICATIONS

D. J. Brown, the Pyrimidines, 1962, pp. 289–291, 359–360.
March, Advanced Organic Chemistry, 3rd Edition, 1985, pp. 334–335.
Kinoshita et al., Biochem. Biophys. Acta 158, 472–475 (1968).
Bubranski et al., CA96-142888b.
Mitsui Toatsu Chemicals, Inc. CA97-110029b.
Vainilavicius et al., CA105-191119q.

Primary Examiner—Mukund J. Shah
Assistant Examiner—Cecilia Shen
Attorney, Agent, or Firm—Walter Patton

[57] ABSTRACT

Disclosed herein are 2,4-disubstituted-5-cyano-1,6-dihydro-6-oxo-1-pyrimidineacetic acids and pharmaceutically acceptable salts thereof and methods of their preparation. The compounds are new aldose reductase inhibitors useful for the treatment or prevention of diabetic complications.

1 Claim, No Drawings

2,4-DISUBSTITUTED-5-CYANO-1,6-DIHYDRO-6-OXO-1-PYRIMIDINEACETIC ACID ALDOSE REDUCTASE INHIBITORS

This is a division of copending application Ser. No. 061,831, filed June 12, 1987, now U.S. Pat. No. 4,786,638.

BACKGROUND OF THE INVENTION

This invention relates to 2,4-disubstituted-5-cyano-1,6dihydro-6-oxo-1-pyrimidineacetic acids, to pharmaceutical salts thereof, to the processes for their preparation, and to methods for using these compounds. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting logevity of diabetic patients has led to complications such as neuropathy, nephropathy, retinopathy, cataracts, and atherosclerosis. These complications have been linked to the undesirable accumulation of sorbitol in diabetic tissue, which inturn results from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators (see J. H. Kinoshita et al, Biochem. Biophys. Acta, 158,472 (1968) and references cited therein) have demonstrated that aldose reductase plays a central role in the etiology of galactosemic cataracts by effecting the conversion of galactose to dulcitol (galactitol); and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord, and kidney of diabetic animals, (see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970)).

N-[[6-Methoxy-5-(trifluoromethyl)-1-naphthalenyl]-thioxomethyl]-N-methylglycine has been reported to be an effective inhibitor of aldose reductase, see K. Sestanj et al, U.S. Pat. No. 4,568,693, Feb. 4, 1986. The present invention discloses novel 2,4-disubstituted-5-cyano-1,6-dihydro-6-oxo-1-pyrimidineacetic acids which unexpectedly show adlose reductase inhibitory activity. Up to now, amino-pyrimidine derivatives have been reported to be useful for increasing cardiac contractility, see J. Bagli et al, U.S. Pat. Nos. 4,505,910, March 19, 1985, and 4,617,393, Oct. 14, 1986.

SUMMARY OF THE INVENTION

The 2,4-disubstituted-5-cyano-1,6-dihydro-6-oxo-1-pyrimidineacetic acids of this invention are represented by formula (I)

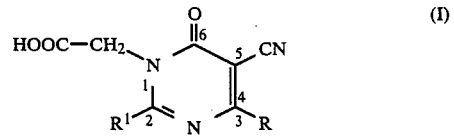

wherein $R^1$ is lower alkyl containing 1 to 3 carbon atoms, cyclo(lower)alkyl containing 3 to 6 carbon atoms, naphthalenyl, or halogen substituted naphthalenyl; R is —$SR^2$ wherein $R^2$ is lower alkyl containing 1 to 6 carbon atoms, phenylmethyl, halogen substituted phenylmethyl, cyclohexylmethyl; or R is

wherein $R^3$ is hydrogen, and $R^4$ is phenylalkyl, pyrindinylmethyl, cyclohexylmethyl; or $R^3$ and $R^4$ are joined together to form piperidinyl, 4-phenylmethylpiperidinyl, or N-phenylmethylpiperazinyl; or R is $R^5$ wherein $R^5$ is lower alkyl containing 1 to 3 carbon atoms, phenyl, or naphthalenylmethyl; and the pharmaceutically acceptable salts thereof.

A preferred aspect of the present invention is the compounds of formula (I) wherein $R^1$ is methyl, isopropyl, cyclohexyl, 1-naphthalency, or 5-bromo-1-naphthalenyl; R is —$SR^2$ wherein $R^2$ is methyl, isopropyl, n-hexyl, phenylmethyl, 4-bromophenylmethyl, or 4-bromo-2-fluorophenylmethyl; or R is

wherein $R^3$ is hydrogen and $R^4$ is phenylmethyl, or phenylethyl; or R is $R^5$ wherein $R^5$ is methyl, phenyl, 1-naphthalenylmethyl; and the pharmaceutically acceptable salts thereof.

A still further preferred aspect of the present invention is the compounds of formula (I) wherein $R^1$ is methyl, cyclohexyl, or 1naphthalenyl; R is —$SR^2$ wherein $R^2$ is methyl, isopropyl, phenylmethyl, or 4-bromo-2-fluorophenylmethyl; or R is

wherein $R^3$ is hydrogen and $R^4$ is phenylmethyl; or R is $R^5$ wherein $R^5$ is methyl, phenyl, or 1-naphthalenylmethyl; and the pharmaceutically acceptable salts thereof.

The most preferred compounds of the present invention are 4-[[(4-bromo-2-fluorophenyl)methyl]thio]-5-cyano-2-cyclohexyl-1,6-dihydro-6-oxo-1-pyrimidineacetic acid; 5-cyano-2-cyclohexyl-1,6-dihydro-4-(methylthio)-6-oxo-1-pyrimidineacetic acid; and 5-cyano-1,6-dihydro-4-methyl-2-(1-naphthaleny)-6-oxo-1pyrimidineacetic acid; and the pharmaceutically acceptable salts thereof.

Included in the present invention are the 2,6-disubstituted-5-cyano-1,4-dihydro-4-oxo-1-pyrimidineacetic acid compounds of formula (I')

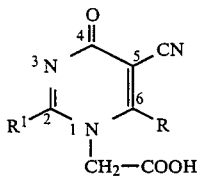

(I')

wherein R and R¹ are as defined above.

The 2,4-disubstituted-5-cyano-1,6-dihydro-6oxo-1-pyrimidineacetic acids, and the pharmaceutically acceptable salts thereof can be prepared by the processes described hereinafter.

A method is provided for preventing or relieving diabetes mellitus associated complications in a diabetic mammal by administering to said mammal a phophylactic or alleviating amount of a compound of formula (I). Such complications include neuropathy, nephropathy, retinopathy, and cataracts.

The compounds of formula (I), when admixed with a pharmaceutically acceptable carrier, form a pharmaceutical composition which can be used according to the preceding method.

DETAILED DESCRIPTION OF THE INVENTION

The compounds of formula (I) form salts with suitable therapeutically acceptable inorganic and organic bases. These derived salts possess the same activity as their parent acid and are included within the scope of this invention. The acid is transormed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates, or bicarbonates of the therapeutically acceptable alkali metals or alkaline earth metals, for example, sodium, potassium, magnesium, calcium, and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di- and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsturated bases containing up to six carbon atoms, such as pyrrolidine, piperidine, morpholine, piperazine, and their N-alkyl and N-hydroxyalkyl derivatives, such as N-methyl-morpholine and N-(2hydroxyethyl)-piperidine, as well as pyridine. Furthermore, there may be mentioned the corresponding quaternary salts, such as the tetraalkyl (for example, tetramethyl), alkyl-alkanol (for example, methyltriethanol and trimethyl-monoethanol), and cyclic ammonium salts, for example, the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible,inert organic solvent, for example, methanol, ethanol, dioxane, and the like in the presence of water. For example, such use of sodium hydroxide, sodium carbonate, or sodium bicarbonate gives a solution of the sodium salt. Evaporation of the solution or addition of a water-miscible solvent of a more moderate polarity, for example, a lower alkanol, for instance, butanol, or a lowre alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether, and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The 2,3-disubstituted -5-cyano-1,6-dihydro-6oxo-1-pyrimidineacetic acids amd the pharmaceutically acceptable salts thereof of this invention may be administered to mammals, for example, man, monkeys, or dogs, either alone or combined with pharmaceutically acceptable excipients, in dosage forms, i.e., capsules or tablets.

Preferably, the compounds of this invention may be given orally. However, the method of administering the present active ingredients of this invention is not to be construed as limited to a particular mode of administration. For example, the compounds may be administered topically directly in the eye in the form of drops of sterile, buffered ophthalmic solutions, preferably of pH 7.2–7.6. Also, they may be administered orally in solid form containing such excipients as starch, milk sugar, certain types of clay, and so forth. They may also be administered orally in the form of solutions or they may be injected parenterally. For parenteral administration they may be used in the form of a sterile solution, preferably of pH 7.2–7.6, containing a pharmaceutically acceptable buffer.

The dosage of the 2,4-disubstituted-5-cyano-1,6-dihydro-6-oxo-1-pyrimidineacetic acids and the pharmaceutically acceptable salts thereof will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05–1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills, and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either efferfvescent or noneffervescent, can contain between about 25 to 1250 mg of the active ingredients of this invention together with conventional pharmaceutical carriers. Thus, tablets, which may be coated and either effervescent or noneffervescent, may be prepared according to the known art. Inert diluents or carriers, for example, magnesium cabonate or lactose, can be used together with conventional disintegrating agents, for example, starch.

The 2,4-disubstituted -5-cyano-1,6-dihydro-6-oxo-1-pyrimidinaecetic acids and the pharmaceutically acceptable salts thereof can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide, and phenformin, are suitable. The compounds herein can be administered sequentially or simultaneously with insulin or the oral hypoglycemic agent. Suitable methods of administration, compositions, and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the 2,4disubstituted-5-cyano-1,6-dihydro-6-oxo-1-pyrimidineacetic acids and the pharmaceutically acceptable salts thereof are administered as described previously. The 2,4-disubstituted-5-cyano-1,6-dihydro-6-oxo-1-pyrimidineacetic acids and the pharmaceutically acceptable salts thereof can be administered with an oral hypoglycemic agent in the form of a pharmaceutical composition comprising effective amounts of each agent.

The aldose reductase inhibiting property of the compounds of this invention and the utilization of the compounds in preventing, diminishing, and alleviating diabetic complications are demonstrable in experiments using galactosemic rats, see Dvornik et al, Science, 182, 1146 (1973). Such experiments are exemplified hereinbelow after the listing of the following general comments pertaining to these experiments:

Male Sprague-Dawley rats, weighing approximately 90 grams were separated into groups of equal average body weight, with six animals per group. The animals were housed in cages of six animals each and maintained on 12 hour night/12 hour day cycles. Except as otherwise noted, the animals were given food and water ad libitum.

On day 1, the galactosemic control group and all drug-treated groups were given access to 20% galactose chow (Bio-serv, Frenchtown, N.J.). Animals in the control group were given access to 20% glucose chow (Bio-Serv). Test compounds were administered either in the diet or by gavage as a suspension in 2% Tween 80 in saline. In experiments in which gavage dosing was used, the animals were administered the test compound daily at approximately the same hour each day. Food intake and body weight were determined twice during the course of the experiment. In cases in which the compound was administered in the diet, the average dose was calculated on the basis of the actual average food intake during the experiment.

On the morning of day 5, all animals were fasted; beginning two hours later the animals were decapitated and the lenses, sciatic nerves, and a 50–100 mg portion of the diaphragm were removed, weighed, and frozen in porcelain plates on dry ice.

The polyol determination was performed by a modification of the procedure of M. Krami et al, Clin. Biochem., 2,373 (1969). Only two minor reagent changes were made: (a) the rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.]

The aldose reductase inhibiting effects of the compounds of formula (I) were also tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens.

The following tabulated results show that the 2,4-disubstituted-5-cyano-1,6dihydro-6-oxo-1-pyrimidineacetic acids of this invention show the property that they diminish the accumulation of galactitol in the lenses and sciatic nerves of rats fed galactose. The figures under L, N and D represent the percentage decrease of galactitol accumulation in the tissues of the lens, sciatic nerve, and diaphragm, respectively, for treated rats as compared to untreated rats.

The last entry in the tables is the compound N-[[6-methoxy-5-(trifluoromethyl)-1-naphthalenyl]-thioxomethyl]-N-methylgylcine. The latter compound is also known as tolrestat. (See U.S. Pat. No. 4,568,693.)

TABLE 1

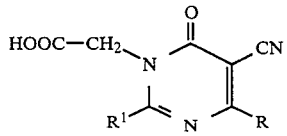
(I)

| Test Compound Example No. | R¹ | R | % Inhibition IN VITRO | | | % Lowering dulcitol accumulation IN VIVO | | | | Melting Point °C. |
|---|---|---|---|---|---|---|---|---|---|---|
| | | | $10^{-5}$ M | $10^{-6}$ M | $10^{-7}$ M | mg/kg | L | N | D | |
| 1 | cyclohexyl | —S—CH₃ | 98 | 94 | 89 | 90 | N.S. | 47 | 42 | 198–199 |
| 2 | " | —S—CH₂—C₆H₅ | 97 | 96 | 91 | 128 | N.S. | N.S. | N.S. | 156–158 |
| 3 | " | —S—CH₂—C₆H₄—Br | 96 | 96 | 93 | 141 | N.S. | N.S. | N.S. | 184–185 |
| 4 | " | —S—CH₂—C₆H₃(F)(Br) | 96 | 94 | 92 | 93 | 15 | 50 | N.S. | 183–184 |
| 5 | " | —S—n-C₆H₁₃ | 94 | 95 | 96 | 121 | N.S. | N.S. | N.S. | 128–129 |
| 6 | cyclohexyl | —S—i-propyl | 93 | 92 | 90 | 110 | N.S. | N.S. | N.S. | 197–200 |
| 7 | " | —S—CH₂—cyclohexyl | 96 | 95 | 90 | 123 | N.S. | N.S. | N.S. | 160–161 |
| 8 | i-propyl | —S—CH₃ | 96 | 96 | 94 | 87 | N.S. | N.S. | N.S. | 226–228 |
| 9 | i-propyl | —S—i-propyl | 96 | 97 | 91 | 92 | N.S. | 38 | 16 | 192.5–193.5 |
| 10 | i-propyl | —S—CH₂—C₆H₅ | 96 | 98 | 94 | 102 | N.S. | N.S. | 38 | 194–195 |

The compounds of TABLE 1 are produced by Process 1 set forth below.

TABLE 1A

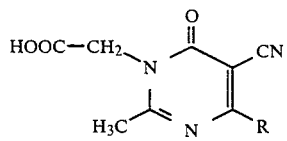
(I)

| Test Compound Example No. | R | % Inhibition IN VITRO | | | % Lowering dulcitol accumulation IN VIVO | | | | Melting Point °C. |
|---|---|---|---|---|---|---|---|---|---|
| | | $10^{-5}$ M | $10^{-6}$ M | $10^{-7}$ M | mg/kg | L | N | D | |
| 11 | —S—CH₃ | 86 | 84 | 74 | 71 | N.S. | N.S. | N.S. | 236–238 |

TABLE 1A-continued

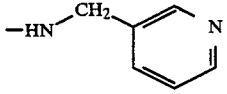

(I)

| Test Compound Example No. | R | % Inhibition IN VITRO | | | % Lowering dulcitol accumulation IN VIVO | | | | Melting Point °C. |
|---|---|---|---|---|---|---|---|---|---|
| | | $10^{-5}$ M | $10^{-6}$ M | $10^{-7}$ M | mg/kg | L | N | D | |
| 12 | 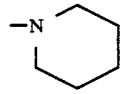 | 88 | 90 | 30 | 84 | N.S. | N.S. | N.S. | 300 |
| 13 | 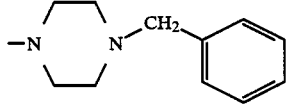 | 88 | 75 | 52 | 93 | N.S. | N.S. | N.S. | 229–230 |
| 14 | 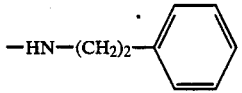 | 92 | 89 | 64 | 112 | N.S. | N.S. | N.S. | 276–278 |
| 15 | —HN—(CH$_2$)$_2$— 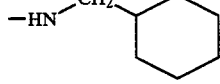 | 89 | 88 | 71 | 98<br>196 | N.S.<br>N.S. | N.S.<br>N.S. | N.S.<br>N.S. | 238–240 |
| 16 | 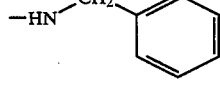 | 93 | 91 | 72 | 100 | N.S. | N.S. | N.S. | 290 |
| 17 | 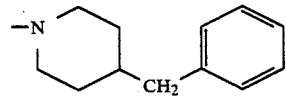 | 96 | 90 | 78 | 100 | N.S. | 33 | N.S. | 222–224 |
| 18 | 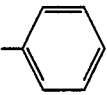 | 90 | 88 | 81 | 128 | N.S. | N.S. | N.S. | 183–184 |

The compounds of TABLE 1A are produced by Process 1A set forth below.

TABLE 2

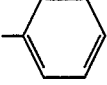

(I)

| Test Compound Example No. | R$^1$ | R | % Inhibition IN VITRO | | | % Lowering dulcitol accumulation IN VIVO | | | Melting Point °C. |
|---|---|---|---|---|---|---|---|---|---|
| | | | $10^{-5}$ M | $10^{-6}$ M | $10^{-7}$ M | mg/kg | L | N | D | |
| 19 | 1-naphthalenyl | phenyl | 84 | 68 | 29 | 117 | N.S. | N.S. | 21 | 234.5–236 |
| 20 | 5-Br—1-naphthalenyl | phenyl | 82 | 71 | 22 | 140 | N.S. | N.S. | N.S. | 234–236 (dec.) |

TABLE 2-continued

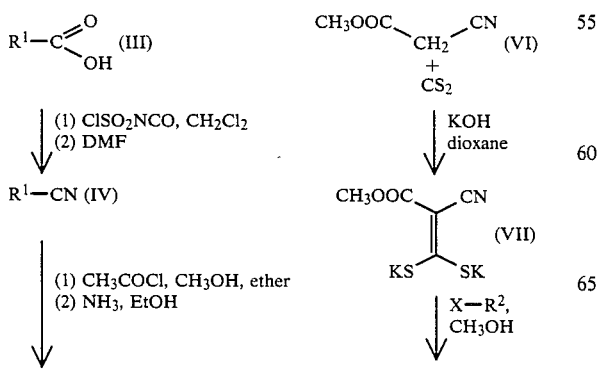
(I)

| Test Compound Example No. | R¹ | R | % Inhibition IN VITRO | | | % Lowering dulcitol accumulation IN VIVO | | | | Melting Point °C. |
|---|---|---|---|---|---|---|---|---|---|---|
| | | | $10^{-5}$ M | $10^{-6}$ M | $10^{-7}$ M | mg/kg | L | N | D | |
| 21 | 1-naphthalenyl | —CH₃ | 87 | 55 | 14 | 103 | 18 | N.S. | N.S. | 234.5–237 (dec.) |
| 22 | 5-Br—1-naphthalenyl | 1-naphthalenyl methyl | 93 | 85 | 46 | 151 | N.S. | 30 | N.S. | 192–193 |
| N—[[6-methoxy-5-(trifluoromethyl)-1-naphthalenyl]thioxomethyl]-N—methylglycine (tolrestat) U.S. Pat. No. 4,568,693 | | | 98 | 94 | 65 | 6 | N.S. | 53 | 90 | 164–165 |

N.S. = not significant
The compounds of TABLE 2 are produced by Process 2 set forth below.

THE PROCESS

The 2,4-disubstituted-5-cyano-1,6-dihydro-6-oxo-1-pyrimidineacetic acids of the present invention were produced by Process 1) condensation of suitable amidines (V) with β, β-bisthioalkyl-α-cyanoacrylic acid methyl esters (VIII) to produce the pyrimidines (IX); Process 1A) displacement of the thiomethyl group of pyrimidineacetic acid esters (XII) made by Process 1 with a primary or secondary amine

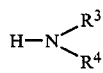

wherein R³ and R⁴ are defined as above to produce the pyrimidines (XIII); and Process 2) condensation of cyanoacetamides (XIX) with N-acyliminoethers (XVIII) to produce the pyrimidines (XX). N-Alkylations of (IX) and (XX) were carried out with X—CH₂—COOR⁶ wherein R⁶ is lower alkyl, and X is bromine, or iodine; preferably with methyl or t-butyl bromoacetates to produce the pyrimidine esters (X) and (XXI); and finally hydrolysis of (X), (XIII), and (XXI) lead to the desired compounds of formula (I).

PROCESS 1

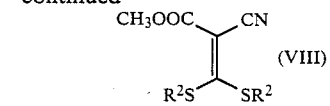

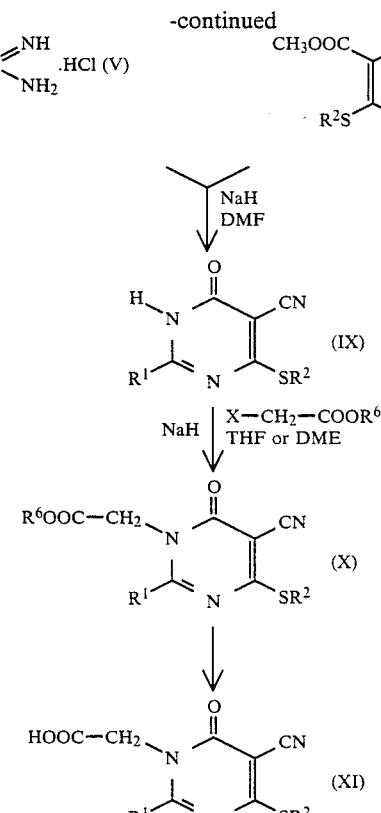

wherein R¹ and R² are as defined above; R⁶ is lower alkyl containing 1 to 4 carbon atoms; and X is bromine, or iodine.

PROCESS 1A

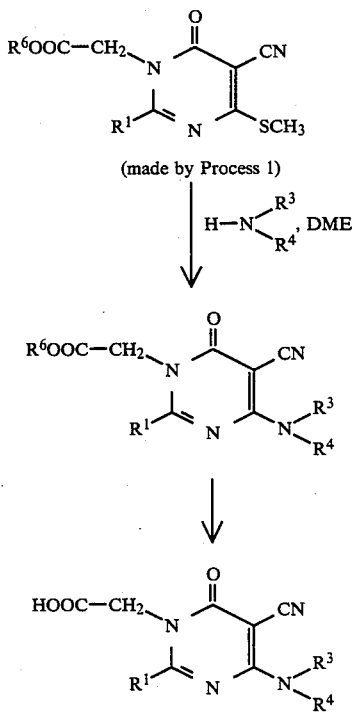

wherein $R^1$, $R^3$, $R^4$, and $R^6$ are as defined above.

PROCESS 2

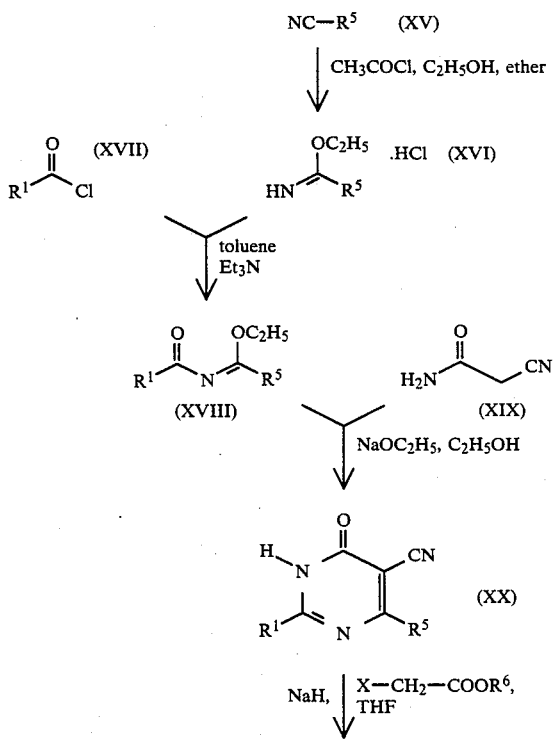

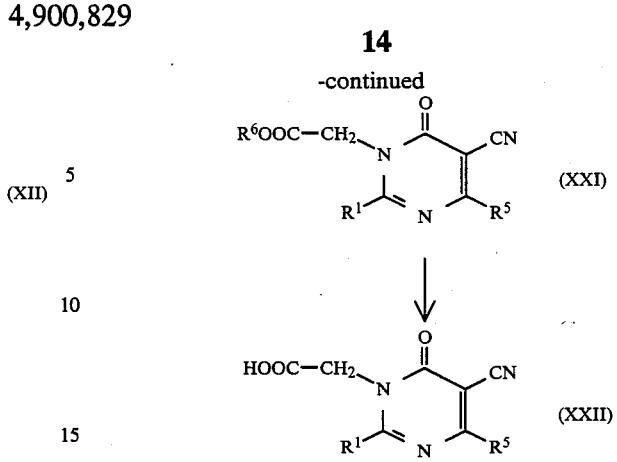

wherein $R^1$, $R^5$, $R^6$, and X are as defined above.

Referring to Process 1, the required amidines (V) were obtained from the corresponding nitriles (IV) in two steps via iminoethers as described in P. E. Fanta et al, J. Am. Chem. Soc., 78, 1434 (1956). However, preparation of naphthalenyl amidine as reported in L. Weintraub, J. Org. Chem., 33, 1679 (1968), via the iminoether of naphthalenyl-1-carboxamide was not reproducible in our hands. The reaction yielded either the starting material or naphthalenyl-1-carbonitrile. The naphthalene moiety was introduced using the alternative synthesis described in Process 2. The required β, β-bisthioalkyl-α-cyanoacrylic acid methyl esters (VIII) in Process 1 were prepared using the general process reported in K. A. Jensen et al, Acta Chem. Scand., 22, 1107 (1968), for the reaction of carbon disulfide with active methylene containing compounds (VI) to produce the compounds (VII), followed by alkylation.

Referring to Process 2, the nitriles (XV) were transformed to the corresponding iminoethers (XVI). Condensation of these iminoethers (XVI) with an acyl chloride (XVII) led to the N-acylimidates (XVIII). These compounds, on condensation with cyanoacetamide (XIX), according to J. L. Soto et al, J. Chem. Soc. Perkins Trans I., 2447 (1984), led to suitably substituted pyrimidines (XX).

In both Process 1 and 2, alkylation of pyrimidines (IX) and (XX), respectively, was effected using sodium hydride as a base in the presence of suitable solvents. It was observed that the proportion of N- and O-alkylated products can be controlled by the choice of the solvent used for the reaction. Thus, using tetrahydrofuran (THR), or dimethoxyethane (DME), it was possible to preferentially obtain N-alkylation, whereas use of dimethylformamide (DMF) as a solvent led to O-alkylation as a preponderant product.

The alkylation could be affected either by using methyl bromoacetate or tbutyl bromoacetate.

The structure of the products of formula (I) was assigned based on the following observations.

(1) The infrared spectra showed a second carbonyl absorption band at 1640–1690 cm$^{-1}$, in addition to the carbonyl due to carboxylic acid.

(2) The —N—CH$_2$—signal characteristic in the NMR.

(3) The lower $R_f$ on the thin layer chromatography relative to the O-alkylated isomers.

The regio-assignment of 1N-alkylation is tentative. The alternative 3N-alkylated structure for the compounds of formula (I) cannot be ruled out because of the

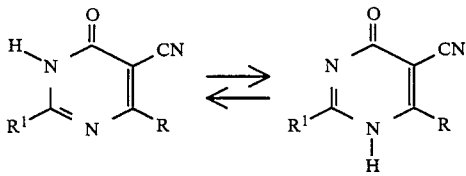

possible tautomerism shown in the equation above.
Accordingly, the compounds of formula (I)

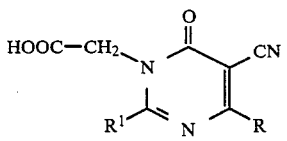

may have the structure (I')

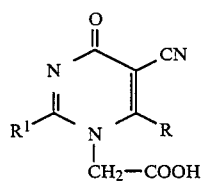

wherein R and R[1] are as defined above.
The following Examples further illustrate this invention.

EXAMPLE 1

(Process 1)

5-Cyano-2-cyclohexyl-1,6-dihydro-4-(methylthio)-6-oxo-1-pyrimidineacetic Acid

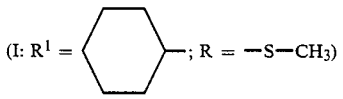

Step (1) Preparation of Cyclohexylcarbonitrile

According to the procedure of G. Lohaus, Chem. Ber., 100, 2719 (1967), to a cooled (0° C.), magnetically stirred solution of cyclohexyl carboxylic acid (113.8 g, 0.89 mol) in methylene chloride (300 mL) was added chlorosulfonylisocyanate, $ClSO_2NCO$, (85.5 mL, 0.98 mol) dropwise. The solution was refluxed 15 minutes and then cooled to room temperature. The ice bath was replaced and DMF (151.3 mL, 1.95 mol) was added dropwise. The ice bath was removed and the resulting yellow solution was stirred at room temperature overnight. The solution was poured onto ice water. The organic layer was washed with saturated $NaHCO_3$, and NaCl solutions and dried with $MgSo_4$. Methylene chloride ($\approx$300 mL) was removed by distillation at atmospheric pressure through a 20 cm Vigreaux column. The crude material remaining was distilled through the same column at reduced pressure. It was collected as a colorless liquid b.p. 83°–86° C./20 mm Hg (77.6 g, 81%).

Step (2) Preparation of Cyclohexylamidine Hydrochloride

To a cooled (0° C.), magnetically stirred solution of cyclohexylcarbonitrile (77.6 g, 0.71 mol), dry methanol (63.4 mL, 1.56 mol), and ether (50 mL) was added acetyl chloride (60.7 mL, 0.85 mol) dropwise. After the addition, cooling was continued for 15 minutes. The mixture was stirred at room temperature for 2 days. The resulting white crystals were filtered, washed with ether, and dried in vacuo. After drying, the crystals were combined with 10% $NH_3$/ethanol (420 mL, 2.46 mol) and stirred at room temperature for 3 days. The solution was filtered, and the filtrate concentrated to yield the product as white needles (84.8 g, 745) m.p. 178°–180° C.

NMR (DMSO-$d_6$): δ 1.45 (m, 10H), 2.40 (t, 1H,), 8.76 (br s, 3H,)

Step (3) Preparation of 2-Cyclohexyl-1,6-dihydro-4-(methylthio)-6-oxo-5-pyrimidinecarbonitrile According to the procedure of U.S. Pat. No. 4,505,910, to a cooled (0° C.), stirred suspension of NaH (50% dispersion inmineral oil, washed with hexane, 5.4 g. 0.113 mol) in DMF (50 mL) was added a solution of cyclohexylamidine hydrochloride (15.2 g, 0.094 mol) in DMF (100 mL). After 1 hour, a solution of 2-cyano-3,3-bis(methylthio)-2-propenoic acid methyl ester [described by R. Gompper et al, Chem. Ber., 95, 2861 (1962)] (19.1 g, 0.094 mol) in DMF (100 mL) was added dropwise. The cooling bath was removed after 1 hour and the reaction mixture was stirred at room temperature overnight. Water (250 mL) and concentrated HCl (10 mL) were added, and the resulting precipitate was collected by filtration. The yellow solid (19.1 g, 82%) was dried and used without further purification.

NMR (DMSO-$d_6$): δ 1.53 (m, 10H), 2.63 (s, 3H), 2.87 (m, 1H)

Step (4) Preparation of Methyl 5-Cyano-2cyclohexyl-1,6-dihydro-4-(methylthio)-6-oxo-1-pyrimidineacetate To a cooled (0° C.), stirred suspension of NaH (50% dispersion in mineral oil, washed with hexane, 2.2 g, 0.047 mol) in DME (350 mL) was added 2-cyclohexyl-1,6-dihydro-4-(methylthio)-6-oxo-5-pyrimidinecarbonitrile (9.5 g, 0.038 mol) in several portions. After 1 hour, methyl bromoacetate was added and the resulting solution was heated at 95°–100° C. for 2 days. The solution was cooled and water (300 mL) was added. The mixture was extracted with ethyl acetate and the combined extracts were washed with water, dried ($MgSO_4$), and concentrated to give a beige powder (12.2 g, 99%) which was used without further purification.

NMR (CDCl$_3$): δ 1.55 (m, 10H), 2.62 (s, 3H), 2.45 (m, 1H), 3.81 (s, 3H), 4.84 (s, 2H)

Step (5) Preparation of 5-Cyano-2-cyclohexyl-1,6-dihydro-4-(methylthio)-6-oxo-1-pyrimidineacetic Acid To a stirred solution of methyl 5-cyano-2-cyclohexyl-1,6-dihydro-4-(methylthio)-6-oxo-1-pyrimidineacetate (4.0 g, 0.012 mol) in dioxane (40 mL) was added 1 N NaOH (14.0 mL, 0.014 mol). After 1.5 hours, the mixture was concentrated, then diluted with water (150 mL). The aqueous solution was washed with ether and acidified with 1 N HCl (16.0 mL, 0.016 mol). The resulting mixture was extracted with ethyl acetate, and the combined extracts were dried ($MgSO_4$), and concentrated. The crude product was recrystallized from acetonitrile (three times) to yield white crystals (1.8 g, 475) m.p. 198°–199° C.

NMR (DMSO-$d_6$): δ 1.51 (m, 10H), 2.62 (s, 3H), 2.85 (m, 1H), 4.82 (s, 2H)

IR (KRb): 2230, 1760, 1640 cm$^{-1}$

UV (MeOH): 240 (19,500), 287 (11,654), 318.5 (8,196)

MS (m/e): 307, 252 (100%), 82

Anal. Calcd.: C, 54.71; H, 5.57; N, 13.675

Found: C, 54.61; H, 5.42; N, 13.87%

EXAMPLE 11

(Process 1)

5-Cyano-1,6-dihydro-2-methyl-4-(methylthio)-6-oxo-1-pyrimidineacetic Acid (I: $R^1$=—$CH_3$; R=—S—$CH_3$)

Step (1) Preparation of Methyl 5-Cyano-1,6-dihydro-2-methyl-4-(methylthio)-6-oxo-1-pyrimidineacetate To a cooled (0° C.), stirred suspension of NaH (50% dispersion in mineral oil, washed with hexane, 5.0g, 0.105 mol) in DMF (70 mL) was added 1,6-dihydro-2-methyl-4-(methylthio)-6-oxo-5-pyrinidinecarbonitrile (prepared by the process of J. Bagli, U.s. Pat. No. 4,505,910, Example 1) (18.1 g, 0.100 mol) in several portions. After 30 minutes, methyl bromoacetate was added and the resulting mixture was stirred at room temperature for 4.5 hours. A little water was added and most of the DMF was removed under reduced pressure. The residue was partitioned between water (150 mL) and chloroform (100 mL), and the organic phase was dried ($MgSO_4$), and concentrated. The crude product was triturated with ether (100 mL) to give the produce (18.5 g, 73%) m.p. 150°-152° C. A portion of the crude product (2.0 g) was recrystallized (twice) from chloroform/hexane to give pure product (1.6 g).

NMR ($CDCl_3$): δ 2.58 (s, 3H), 2.65 (s, 3H), 3.85 (s, 3H), 4.83 (s, 2H)

IR ($CHCl_3$): 2240, 1760, 1690 $cm^{-1}$

UV (MeOH): 240 (18,371), 285 (10,989), 317 (7,571)

MS (m/e): 253($M^+$), 222, 194

Anal. Calcd.: C, 47.43; H, 4.34; N, 16.60%

Found: C, 47.13; H, 4.29; N, 16.24%

Step (2) Preparation of 5-Cyano-1,6-dihydro-2-methyl-4-(methylthio)-6-oxo-1-pyrimidineacetic Acid To a suspension of methyl 5-cyanob 1,6-dihydro-2-methyl-4-(methylthio)-6-oxo-1-pyrimidineacetate (2.3 g, 9.0 mmol) in methanol (6 mL) was added 3 N NaOH (3.3 mL, 9.9 mmol). The mixture was warmed to 30° C. for 1.5 hours, then concentrated to remove the methanol. The residue was dissolved in water (20 mL) and neutralized with 3 N HCl (3.3 mL, 9.9 mmol). The resulting precipitate was collected by filtration, and recrystallized from methanol/ether/hexane (twice) to yield pure product (1.5 g, 35%) m.p. 236°-238° C.

NMR (DMSO-$d_6$): δ 2.60 (s, 3H), 2.68 (s, 3H), 4.05 (s, 1H), 4.84 (s, 2H)

IR (NUJOL): 3050, 2230, 1740, 1660 $cm^{-1}$

UV (MeOH): 286 (10,260), 240 (14,216), 213 (13845)

MS (m/e): 239 ($M^+$)

Anal. Calcl.: C, 45.18; H, 3.76; N, 17.57%

Found: C, 45.46; H, 4.00; N, 17.56%

EXAMPLE 12

(Process 1A)

5-Cyano-1,6-dihydro-2-methyl-6-oxo-4-[(3-pyridinylmethyl)amino]-1-pyrimidineacetic Acid

[I: $R^1$=—$CH_3$; R=(3-pyridinylmethyl)amino]

Step (1) Preparation of Methyl 5-cyano-1,6-dihydro-2-methyl-6-oxo-4-[(3-pyridinylmethyl)amino]-1-pyrimidineacetate To a stirred suspension of methyl 5-cyano-1,6-dihydro-2-methyl-4-(methylthio)-6-oxo-1-pyrimidineacetate (prepared by the process of Example 11, Step 1) (0.25 g, 1.0 mm9l) in DME (1 mL) was added 3-methylaminopyridine (0.12 g, 1.1 mmol). The reaction mixture was heated to reflux for 19 hours, additional DME (0.5 mL) was added, and heating was continued for 4 hours. The mixture was then cooled to room temperature, diluted with ether, and filtered to give the produce (0.2 g, 94%).

NMR ($CDCl_3$): δ 2.45 (s, 3H), 3.50 (br s, 2H), 3.85 (s, 3H), 4.75 (m, 3H), 7.40 (m, 1H), 8.60 (m, 2H)

IR ($CHCl_3$): 2100, 1735, 1660 $cm^{-1}$

Step (2) Preparation of 5-Cyano-1,6-dihydro-1-methyl-6-oxo-4-[(3-pyridinylmethyl)amino]-1-pyrimidineacetic Acid To a suspension of methyl 5-cyano-1,6-dihydro-2-methyl-6-oxo-4-[(3-pyridinylmethyl)amino]-1-pyrimidineacetate (1.5 g, 5.0 mmol) in methanol (5 mL) was added 3 N NaOH (1.8 mL, 5.5 mmol). The resulting mixture was warmed to 50° C. for 1.5 hours, cooled, and neutralized with 3 N HCl (1.8 mL, 5.5 mmol). A precipitate formed, and was collected by filtration to give a crude product (1.5 g, 88%). Recrystallization from DMF/methanol (twice) yielded a white solid (1.2 g) m.p. >300° C.

NMR ($CF_3CO_2D$): δ 2.70 (s, 3H), 5.05 (s, 2H), 5.25 (s, 2H), 8.20 (m, 1H), 8.90 (m, 3H)

IR (KBr): 3450, 3275, 3000, 2210, 1660, 1615 $cm^{-1}$

UV (MeOH): 294 (4,883), 270 (6,028), 228 (23,713)

Anal. Calcd.: C, 56.18; H, 4.34: N, 23.42%

Found: C, 55.78; H, 4.51; N, 22.97%

EXAMPLE 20

(Process 2)

5-Cyano-1,6-dihydro-2-(5-bromo-1-naphthalenyl)-6-oxo-4-phenyl-1-pyrimidineacetic Acid (I: $R^1$=5-bromo-1naphthalenyl; R=phenyl)

Step (1) Preparation of Ethyl N-(5-Bromo-1-naphtholy)benzimidate

According to the procedure of Soto et al, Synthesis, 483 (1983), a solution of 5-bromo-1-naphthoyl chloride (10.7 g, 39.8 mmol) in dry toluene (30 mL) was added dropwise to a mixture of ethyl benzimidate hydrochloride (7.4 g, 39.8 mmol) and triethylamine (8.9 g, 12.2 mL, 87.6 mmol) in dry toluene (100 mL). The mixture was stirred for 18 hours at room temperature, then heated to 70° C. for 60 hours. The mixture was cooled to room temperature and the precipitated salt removed by filtration and washed with toluene. The filtrate was concentrated in vacuo to give a red oil which crystallized upon drying in vacuo (15.2 g, quant.). This material was of sufficient purity to be used in the subsequent reaction.

NMR ($CDCl_3$): δ 1.51 (t, 3H, J=6.8Hz), 4.52 (q, 3H, J=6.8Hz), 7.35 (m, 5H), 7.61 (d, 2H, J=7.1Hz), 7.85 (d, 1H, J=7.2Hz), 8.21 (d, 1H, J=7.4Hz), 8.48 (d, 1H, J=8.6Hz), 9.02 (d, 1H, J=8.4Hz)

Step (2) Preparation of 1,6-Dihydro-2-(5-bromo-1-naphthalenyl)-6-oxo-4-phenyl-5-pyrimidinecarbonitrile According to the procedure of Soto et al, J. Chem. Soc. Perkin Trans. I, 2447 (1984), cyanoacetamide (3.4 g, 40 mmol) was added to a suspension of sodium ethoxide, freshly prepared from sodium (1.1 g, 48 mmol) in anhydrous ethanol (75 mL). Ethyl N-(5-bromo-1-naphthoyl)benzimidate (15.3 g, 40 mmol) was added portionwise, and the resulting mixture was heated to reflux for 5 hours. The mixture was allowed to stir at room temperature for 15 hours, neutralized with concentrated $H_2SO_4$ (1.33 mL), and diluted with water (300 mL). The precipitated product was collected by filtration, and washed with water. Recrystallization from ethanol/DMF gave pur product as a yellow solid (10.3 g, 64%), m.p. 328°-330° C.

NMR (DMSO-d$_6$): δ 7.55 (m, 4H), 7.82 (dd, 1H, J$_1$=8.6Hz, J$_2$=8.5Hz), 7.95 (d, 3H, J=8.1Hz), 7.99 (d, 1H, J=7.5Hz), 8.30 (d, 1H, J=8.6Hz), 8.39 (d, 1H, J=8.5Hz), 9.10 (br s, 1H)

IR (KBr): 2225, 1660 cm$^{-1}$

Anal. Calcd.: C, 62.70; H, 3.01; N, 10.45%
Found: C, 62.88; H, 3.39; N, 10.37%

Step (3) Preparation of t-Butyl 5-Cyano-1,6-dihydro-2-(5-bromo-1-naphthalenyl)-6-oxo-4-phenyl-1-pyrimidineacetate 1,6-Dihydro-2-(5-bromo-1-naphthalenyl)-6-oxo-4-phenyl-5-pyrimidinecarbonitrile (4.0 g, 9.9 mmol) was added portionwise to a suspension of sodium hydride (60% dispersion in mineral oil, washed with hexane, 0.6 g, 14.9 mmol) in dry THF (80 mL). After 5 minutes the mixture became a homogeneous solution. Neat t-butyl bromoacetate (2.9 g, 14.9 mmol) was added in one portion and the mixture was refluxed for 18 hours. Additional t-butyl bromoacetate (0.4 g, 2.0 mmol) was added and reflux was continued for 2 hours. The reaction mixture was cooled to room temperature and quenched with water. The mixture was partitioned between water (50 mL) and CHCl$_3$ (100 mL), and the aqueous layer was extracted with CHCl$_3$ (2×50 mL). The combined organic layers were washed with water, brine, dried over Na$_2$SO$_4$, and concentrated in vacuo to give an orange foam (5.4 g). The material was purified by radial preparative thin-layer (Chromatotron) chromatography with elution by EtOAc/hexanes (20:80) to give the pure product (3.0 g, 59%).

NMR (CDCl$_3$): δ 1.38 (s, 9H), 4.10 (d, 1H, J=16.9Hz), 4.77 (d, 1H, J=16.9Hz), 7.40–7.80 (m, 7H), 7.94 (d, 1H, J=9.0Hz), 8.15 (d, 2H, J=7.6Hz), 8.52 (d, 1H, J=8.0Hz)

Step (4) Preparation of 5-Cyano-1,6-dihydro-2-(5-bromo-1-naphthalenyl)-6-oxo-4-phenyl-1-pyrimidineacetic Acid t-Butyl 5-cyano-1,6-dihydro-2-(5-bromo-1-naphthalenyl)-6-oxo-4-phenyl-1-pyrimidineacetate (3.02 g, 5.85 mmol) was dissolved in trifluoroacetic acid (10 mL), and the mixture was stirred at room temperature for 4 hours. The solvent was removed in vacuo and the oily residue was triturated with ether. The ether was removed in vacuo to give a yellow foam which was recystallized twice from EtOAc/hexanes to give the pure product as a white solid (1.28 g, 48%).

NMR (DMSO-d$_6$): δ 4.25 (d, 1H, J=7.1Hz), 4.59 (d, 1H, J=7.1Hz), 7.49 (t, 1H, J=7.4Hz), 7.58 (m, 2H), 7.62 (m, 1H), 7.78 (d, 1H, J=7.1Hz), 7.85 (dd, 1H, J$_1$=8.4Hz, J$_2$=7.4Hz), 7.91 (d, 1H, J=8.3Hz), 7.96 (d, 2H, J=7.0Hz), 8.01 (d, 1H, J=7.4Hz), 8.39 (d, 1H, J=8.0Hz), 9.70 (br s, 1H)

IR (CHCl$_3$): 3420, 2225, 1725, 1695 cm$^{-1}$

Anal. Calcd.: C, 60.02; H, 3.07; N, 9.13%
Found: C, 60.08; H, 3.45; N, 8.90%

We claim:

1. The process for producing the compounds of formula (I)

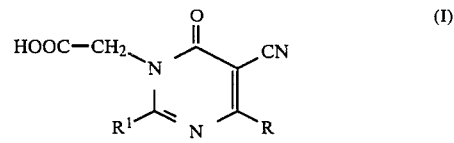

wherein R$^1$ is lower alkyl having 1 to 3 carbon atoms, cyclo(lower)alkyl having 3 to 6 carbon atoms, naphthalenyl, or halogen substituted naphthalenyl; R is —SR$^2$ wherein R$^2$ is lower alkyl having 1 to 6 carbon atoms, phenylmethyl, halogen substituted phenylmethyl, or cyclohexylmethyl or R is R$^5$ wherein R$^5$ is lower alkyl having 1 to 3 carbon atoms, phenyl, or naphthalenymethyl; and the pharmaceutically acceptable salts thereof which comprises N-alkylating the compounds of formula

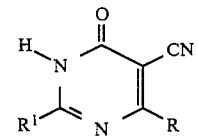

wherein R and R$^1$ are as defined above with X-CH$_2$-COOR$^6$, wherein R$^6$ is lower alkyl having 1 to 4 carbon atoms, and X is bromine or iodine in the presence of the strong base sodium hydride in tetrahydrofuran or dimethoxyethane solvent to produce the compounds of formula

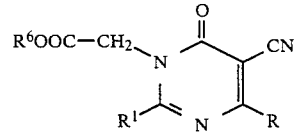

wherein R, R$^1$ and R$^6$ are as defined above and hydrolyzing the ester group of said compound with base to produce the desired compounds of formula (I).

* * * * *